United States Patent
Matsubara et al.

(10) Patent No.: US 6,631,632 B2
(45) Date of Patent: Oct. 14, 2003

(54) INTAKE AIR OXYGEN CONCENTRATION SENSOR CALIBRATION DEVICE AND METHOD

(75) Inventors: Takuji Matsubara, Susono (JP); Mamoru Yoshioka, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 225 days.

(21) Appl. No.: 09/905,929

(22) Filed: Jul. 17, 2001

(65) Prior Publication Data
US 2002/0014103 A1 Feb. 7, 2002

(30) Foreign Application Priority Data

Jul. 26, 2000 (JP) ........................................ 2000-225615

(51) Int. Cl.⁷ .............................................. G01N 27/46
(52) U.S. Cl. ...................................................... 73/1.06
(58) Field of Search ............................... 73/1.06, 118.1, 73/23.31, 23.32; 702/104, 85; 123/494

(56) References Cited

U.S. PATENT DOCUMENTS 4,860,712 A * 8/1989 Nakajima et al. ........... 123/697

FOREIGN PATENT DOCUMENTS

| JP | (P) HEI 10-176577 | 6/1998 |
| JP | (P) HEI 11-002153 | 1/1999 |
| JP | (P) HEI 11-101154 | 4/1999 |

* cited by examiner

Primary Examiner—Robert Raevis
(74) Attorney, Agent, or Firm—Kenyon & Kenyon

(57) ABSTRACT

An intake air oxygen concentration sensor calibration device is provided with an oxygen concentration sensor that detects a concentration of oxygen contained in intake air, intake passageway pressure detection means, stable condition determination means that determines whether the intake passageway pressure is in a stable condition based on the amplitude of fluctuations in intake passageway pressure and a predetermined stable condition criterion value, calibration coefficient calculation means that calculates a calibration coefficient based on the intake passageway pressure and a reference output value of the oxygen concentration sensor, and calibration means that calibrates the output of the oxygen concentration sensor based on the calibration coefficient, wherein and the stable condition criterion value is set so that the smaller the intake passageway pressure detected, the smaller the value, and the greater the intake passageway pressure detected, the greater the value, and the calibration coefficient calculation means updates the calibration coefficient when the intake passageway pressure is stable.

3 Claims, 6 Drawing Sheets

INTAKE AIR OXYGEN CONCENTRATION SENSOR CALIBRATION DEVICE AND METHOD

The disclosure of Japanese Patent Application No. 2000-225615 filed on Jul. 26, 2000 including the specification, drawings and abstract is incorporated herein by reference in its entirety.

BACKGROUND OF THE INVENTION

1. Field of the Invention

The present invention relates to an intake air oxygen concentration sensor calibration device and method that calibrates an output of an oxygen concentration sensor that is provided in a prescribed arrangement along an intake passageway of an internal combustion engine and detects concentration of oxygen contained in intake air.

2. Description of the Related Art

There is available art that is intended to enhance accuracy in control of the air-fuel ratio of internal combustion engines by providing an oxygen concentration sensor in a prescribed arrangement along an intake passageway of the internal combustion engine to detect oxygen concentration in intake air and using the oxygen concentration data detected for controlling operations of the internal combustion engine. One such arrangement is disclosed in Japanese Patent Application Laid-Open Publication No. 11-2153.

The output of the oxygen concentration sensor, however, varies with time and operating conditions (such as engine loads and purge conditions of trapped fuel) of the internal combustion engine. If control is provided for operations of the internal combustion engine, such as air-fuel ratio control, based on variable outputs as those noted above, it is not possible to provide accurate control, which could result in deteriorated exhaust emissions and driveability.

SUMMARY OF THE INVENTION

In view of the foregoing, it is an object of this invention to provide an intake air oxygen concentration sensor calibration device and method that calibrates an output of an oxygen concentration sensor that is provided in a prescribed arrangement along an intake passageway and detects concentration of oxygen contained in intake air, thereby allowing control of high accuracy to be provided.

A first aspect of this invention is an intake air oxygen concentration sensor calibration device that is provided with an oxygen concentration sensor provided in a prescribed arrangement along an intake passageway of an internal combustion engine to detect concentration of oxygen contained in intake air, intake passageway pressure detection means that detects pressure in the intake passageway, stable condition determination means that compares the amplitude of fluctuations in intake passageway pressure detected by the intake passageway pressure detection means with a predetermined stable condition criterion value previously stored in memory to determine whether the intake passageway pressure is in a stable condition, calibration coefficient calculation means that calculates a calibration coefficient used to calibrate the output of the oxygen concentration sensor based on the intake passageway pressure detected by the intake passageway pressure detection means and a reference output value of the oxygen concentration sensor previously stored in memory, and calibration means that calibrates the output of the oxygen concentration sensor based on the calibration coefficient calculated by the calibration coefficient calculation means, wherein the stable condition criterion value is set so that the smaller the intake passageway pressure detected by the intake passageway pressure detection means, the smaller the value is, and the greater the intake passageway pressure detected by the intake passageway pressure detection means, the greater the value is, and the calibration coefficient calculation means updates the calibration coefficient when the stable condition determination means determines that the intake passageway pressure remains stable.

According to the first aspect, the stable condition criterion value is set small when the intake passageway pressure detected by the intake passageway pressure detection means stays in a region of small values (and the stable condition criterion value is set large when the intake passageway pressure detected by the intake passageway pressure detection means stays in a region of large values). This permits a precise determination to be made to determine whether the intake passageway pressure remains stable, that is, whether it is in a condition in which, when the calibration coefficient is to be calculated based on the output of the oxygen concentration sensor, the calculation of the calibration coefficient is less susceptible to effects of errors such as a response lag of the oxygen concentration sensor. Results of detection of greater accuracy can therefore be obtained by calibrating the output of the oxygen concentration sensor by using the calibration means while the intake passageway pressure remains stable (or when the calculation of the calibration coefficient is less susceptible to effects of errors such as a response lag of the oxygen concentration sensor).

A second aspect of this invention is an intake air oxygen concentration sensor calibration device that is provided with an oxygen concentration sensor provided in a prescribed arrangement along an intake passageway of an internal combustion engine to detect concentration of oxygen contained in intake air, intake passageway pressure detection means that detects pressure in the intake passageway, calibration coefficient calculation means that calculates a calibration coefficient used to calibrate the output of the oxygen concentration sensor based on the intake passageway pressure detected by the intake passageway pressure detection means and a reference output value of the oxygen concentration sensor previously stored in memory, and calibration means that calibrates the output of the oxygen concentration sensor based on the calibration coefficient calculated by the calibration coefficient calculation means, wherein the calibration coefficient calculation means stores in memory the intake passageway pressure when the calibration coefficient is updated and updates the calibration coefficient only when the intake passageway pressure detected by the intake passageway pressure detection means is greater than the intake passageway pressure when the calibration coefficient was updated last.

According to this second aspect, an error contained in the output of the oxygen concentration sensor accounts for a smaller percentage of the entire output of the oxygen concentration sensor when the output is greater, and the oxygen concentration sensor has a characteristic that the higher the pressure detected, the higher the output it produces even with the same oxygen concentration. It is therefore possible not to update the calibration coefficient when the intake passageway pressure is smaller than that when the calibration coefficient was updated last, thereby maintaining the last calibration coefficient, which is considered to have greater accuracy. When the intake passageway pressure is greater than that when the calibration coefficient was updated last, on the other hand, it is possible to calculate anew the calibration coefficient that has greater accuracy.

A third aspect of this invention is an intake air oxygen concentration sensor calibration device that is provided with an oxygen concentration sensor provided in a prescribed arrangement along an intake passageway of an internal combustion engine to detect concentration of oxygen contained in intake air, intake passageway pressure detection means that detects pressure in the intake passageway, calibration coefficient calculation means that calculates a calibration coefficient used to calibrate the output of the oxygen concentration sensor based on the intake passageway pressure detected by the intake passageway pressure detection means and a reference output value of the oxygen concentration sensor previously stored in memory, and calibration means that calibrates the output of the oxygen concentration sensor based on the calibration coefficient calculated by the calibration coefficient calculation means. The intake air oxygen concentration sensor calibration device according to the third aspect is further provided with air-fuel ratio detection means that is provided in a prescribed arrangement on an exhaust passageway of the internal combustion engine to detect an exhaust air-fuel ratio of an exhaust gas and calibration coefficient correction means that corrects the calibration coefficient based on an air-fuel ratio feedback correction coefficient calculated from the exhaust air-fuel ratio detected by the air-fuel ratio detection means or the exhaust air-fuel ratio itself detected by the air-fuel ratio detection means.

According to the third aspect, the calibration coefficient calculated based on the intake passageway pressure developing on the intake side of the internal combustion engine is further corrected by using the information obtained based on the exhaust air-fuel ratio on the exhaust side. Calibration of the output of the oxygen concentration sensor according to the calibration coefficient is then corrected through feedback of the information on the exhaust side, which permits calibration of even greater accuracy. The information based on the exhaust air-fuel ratio on the exhaust side may be the exhaust air-fuel ratio itself, or the air-fuel ratio feedback correction coefficient produced as a result of detection made by the air-fuel ratio detection means.

A fourth aspect of this invention is an intake air oxygen concentration sensor calibration device that is provided with an oxygen concentration sensor provided in a prescribed arrangement along an intake passageway of an internal combustion engine to detect concentration of oxygen contained in intake air, intake passageway pressure detection means that detects pressure in the intake passageway, calibration coefficient calculation means that calculates a calibration coefficient used to calibrate the output of the oxygen concentration sensor based on the intake passageway pressure detected by the intake passageway pressure detection means and a reference output value of the oxygen concentration sensor previously stored in memory, and calibration means that calibrates the output of the oxygen concentration sensor based on the calibration coefficient calculated by the calibration coefficient calculation means. The intake air oxygen concentration sensor calibration device according to the fourth aspect is further provided with warm-up completion determination means that determines whether or not the internal combustion engine has completed warming up and the calibration coefficient calculation means updates and stores in memory the calibration coefficient only when the calibration coefficient obtained through calculation is greater than that of the previous update and, at the same time, the warm-up completion determination means determines that the internal combustion engine has completed warming up.

According to the fourth aspect, the calibration coefficient is updated and stored in memory only when an accurate calibration coefficient not affected by blow-by gas is obtained through calculation, which permits calibration of even greater accuracy. The blow-by gas containing unburned fuel can at times be recirculated to an upstream side of the intake passageway. In a condition immediately after a cold internal combustion engine has been started, in which the internal combustion engine still remains cold, however, the concentration of unburned fuel contained in the blow-by gas are so low it is negligible. The fact that the calibration coefficient obtained through calculation is greater than that previously obtained means that the calculation has been made accurately thanks to the intake air not affected by unburned fuel contained in the blow-by gas leaner than in the previous update. Calibration of even greater accuracy can therefore be made by allowing the calibration coefficient to be updated and stored in memory only when the calibration coefficient obtained through calculation is greater than that of the previous update and, at the same time, the warm-up completion determination means determines that the internal combustion engine has completed warming up.

A fifth aspect of this invention is an intake air oxygen concentration sensor calibration device that is provided with an oxygen concentration sensor provided in a prescribed arrangement along an intake passageway of an internal combustion engine to detect concentration of oxygen contained in intake air, intake passageway pressure detection means that detects pressure in the intake passageway, calibration coefficient calculation means that calculates a calibration coefficient used to calibrate the output of the oxygen concentration sensor based on the intake passageway pressure detected by the intake passageway pressure detection means and a reference output value of the oxygen concentration sensor previously stored in memory, and calibration means that calibrates the output of the oxygen concentration sensor based on the calibration coefficient calculated by the calibration coefficient calculation means. The intake air oxygen concentration sensor calibration device according to the fifth aspect is further provided with a fuel storage tank that stores fuel for the internal combustion engine and fuel vapor purge means that traps fuel vapors in the fuel storage tank and supplies it to the intake passageway. The calibration coefficient calculation means replaces the calibration coefficient obtained through calculation with a lower limit guard value pre-stored in memory when the calibration coefficient calculated by the calibration coefficient calculation means while purging of the trapped fuel to the intake passageway by the fuel vapor purge means is not being carried out is the lower limit guard value or less.

According to the fifth aspect, an effect that would be produced if calculation of the calibration coefficient were inaccurate can be minimized. If the calibration coefficient is small, it is possible, however, that the actual output of the oxygen concentration sensor is made small for some reason. It is at the same time possible that the calibration coefficient is not accurately calculated. If the calibration coefficient obtained through calculation is found to be smaller than the lower limit guard value, therefore, the calibration coefficient is replaced with this lower limit guard value, thereby minimizing the effect that would be produced if the calculated calibration coefficient is not accurate.

DETAILED DESCRIPTION OF THE PREFERRED EMBODIMENTS

Figure 1:
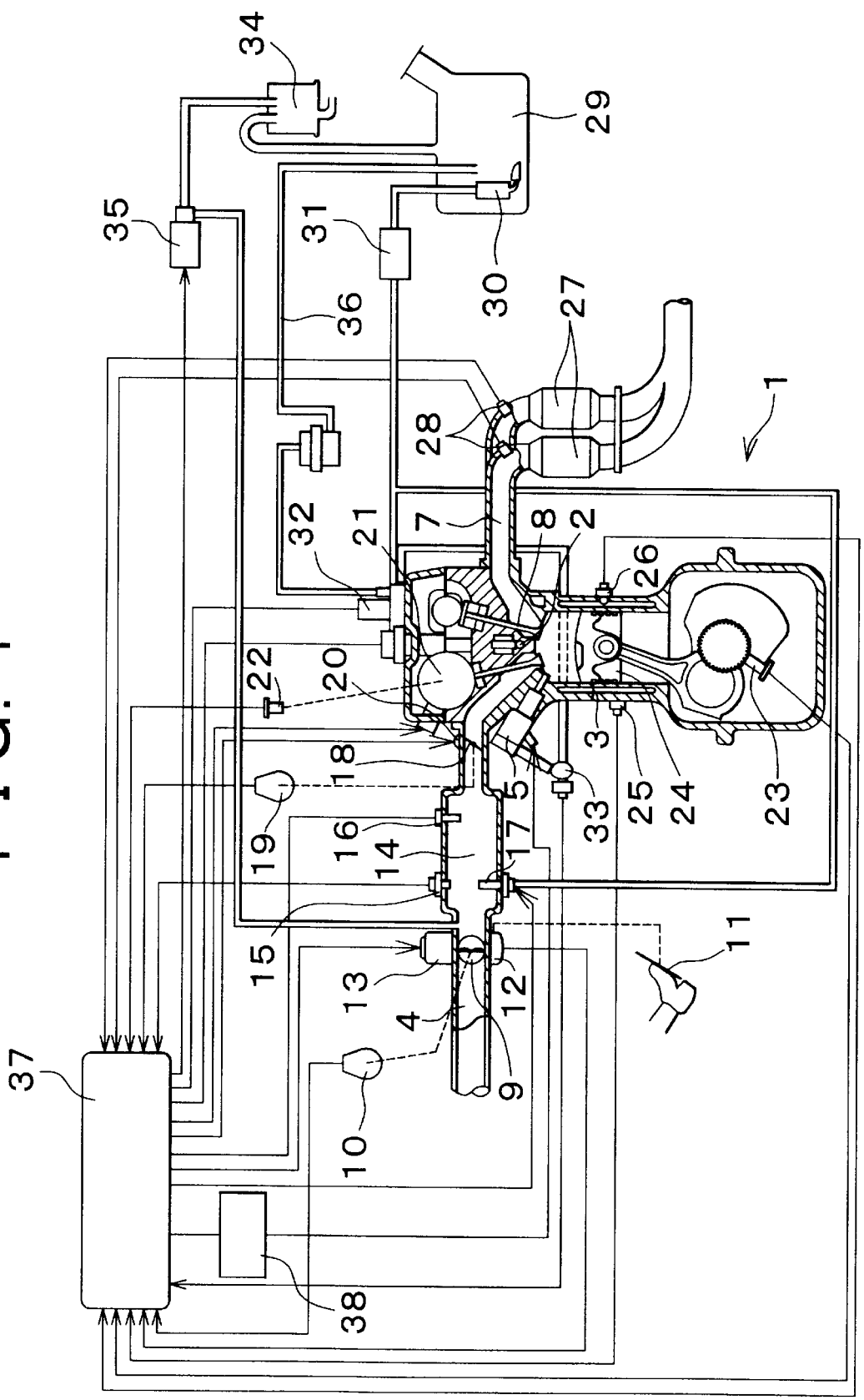
FIG. 1 is a cross-sectional view showing an internal combustion engine having an embodiment of the intake air oxygen concentration sensor calibration device according to this invention.

A preferred embodiment of the intake air oxygen concentration sensor calibration device according to the present invention will hereinafter be described with reference to the drawings. FIG. 1 is a block diagram showing an internal combustion engine having the calibration device according to this embodiment.

An engine 1 serving as the internal combustion engine generates a driving force by letting an ignition plug 2 ignite a mixture in each cylinder 3, as shown in FIG. 1. When there is combustion in the engine 1, air drawn in from an outside passes through an intake passageway 4 and is mixed with fuel injected from an injector 5 to become a mixture. An internal portion of the cylinder 3 is communicated to, and isolated from, the intake passageway 4 by an intake valve 6. The mixture burned in the internal portion of the cylinder 3 is exhausted through an exhaust passageway 7 as exhaust gas. The internal portion of the cylinder 3 is communicated to, and isolated from, the exhaust passageway 7 by an exhaust valve 8.

A throttle valve 9 that varies the amount of air drawn into the cylinder 3 is provided in a prescribed arrangement along the intake passageway 4. A throttle position sensor 10 that detects the opening of the throttle valve is connected to the throttle valve 9. In addition, an accelerator position sensor 12 that detects the position of an accelerator pedal 11 being depressed and a throttle motor 13 that drives the throttle valve 9 accompany the throttle valve 9. There is also installed, though not shown, an intake air temperature sensor that detects the temperature of the intake air along the intake passageway 4.

A surge tank 14 is formed on a downstream side of the throttle valve 9. A vacuum sensor 15, an oxygen concentration sensor 16, and a cold start injector 17 are provided in a prescribed arrangement inside the surge tank 14. The vacuum sensor 15 detects the pressure in the intake passageway 4 (intake passageway pressure), functioning as an intake passageway pressure detection means. The oxygen concentration sensor 16 calculates the oxygen concentration of intake air, varying an output voltage thereof according to a mass ratio or a volume ratio of oxygen contained in the detected gas. The cold start injector 17 is intended to improve cold start performance of the engine 1. It sprays dispersed fuel into the surge tank 14 to form a uniform mixture.

There is provided in a prescribed arrangement a swirl control valve 18 further on the downstream side of the surge tank 14. The engine 1 is a direct injection engine capable of burning a lean mixture. The swirl control valve 18 produces a stable swirl inside the cylinder 3 during lean burn (stratified charge combustion). An SCV position sensor 19 that detects the opening of the swirl control valve 18 and a DC motor 20 that drives the swirl control valve 18 accompany the swirl control valve 18.

The timing at which to open or close the intake valve 6 in the engine 1 according to this embodiment can be variably controlled by a variable valve timing mechanism 21. The opening of the intake valve 6 can be detected by a cam position sensor 22 that detects the position of rotation of a camshaft, on which a cam that opens and closes the intake valve 6 is formed. Moreover, there is installed a crank position sensor 23 that detects the position of rotation of a crankshaft. An output from the crank position sensor 23 also provides information for determining the position of a piston 24 in the cylinder 3 and an engine speed. The engine 1 is also mounted with a knock sensor 25 that detects knocking of the engine 1 and a coolant temperature sensor 26 that detects the temperature of a coolant.

An exhaust emission purification catalyst 27 that purifies harmful substances contained in exhaust gas is mounted along the exhaust passageway 7. The engine 1 has four cylinders and one exhaust emission purification catalyst 27 is provided for each pair of the cylinders, namely, there are a total of two catalysts. An air-fuel ratio sensor 28 that detects an exhaust air-fuel ratio of the exhaust gas is provided for each, and on an upstream side, of the two exhaust emission purification catalysts 27. Typical types of sensors used as the air-fuel ratio sensor 28 include a linear air-fuel ratio sensor that is capable of linearly detecting the exhaust air-fuel ratio covering from a rich zone to a lean zone and an oxygen sensor that is activated or deactivated to determine when the exhaust air-fuel ratio is in a rich zone or a lean zone.

Fuel is supplied to the injector 5 of the engine 1 as follows. Fuel stored in a fuel tank 29 is sent by a fuel-sending low-pressure fuel pump 30 and passes through a fuel filter 31. It is then pressurized by a high-pressure fuel pump 32 before being delivered to the injector 5. The engine 1 is capable of lean burn. This requires that the fuel be formed into a state suitable for stratified charge combustion by directly injecting it into the cylinder 3 on a compression stroke thereof to permit good lean burn (stratified charge combustion). To achieve this end, fuel is pressurized to a high pressure level before being injected by the injector 5.

Associated with the injector 5, there is also provided in a prescribed arrangement a fuel pressure sensor 33 that detects the pressure of fuel to provide precise control. The high-pressure fuel pump 32 makes use of a power driving force of the engine 1, namely, rotation of a camshaft on the side of the exhaust valve 8 to pressurize fuel. Fuel sent by the low-pressure fuel pump 30 is directly supplied to the cold start injector 17.

A charcoal canister 34 that traps fuel vapors in the fuel tank 29 is provided in a prescribed arrangement to accompany the fuel tank 29. The charcoal canister 34 has an activated carbon filter inside that traps fuel vapors. The trapped fuel is controlled for the amount of purge by a purge control valve 35 and purged to the intake passageway 4 before being burned in the cylinder 3. The fuel tank 29 is also mounted with a return pipe 36, through which residual fuel that was not injected is returned to the fuel tank 29.

In addition, the engine 1 also has a built-in blow-by gas reduction system that is, though not shown, mounted in virtually all late-model engines. The blow-by gas reduction system functions to recirculate blow-by gas that contains unburned fuel which has escaped to the bottom of the cylinder 3 during a compression stroke back up along the intake passageway 4. The point of recirculation varies depending on engine load (C) (intake passageway pressure) and other factors. The blow-by gas may be recirculated to the intake port or to the upstream side of the throttle valve 9.

The ignition plug 2, injector 5, throttle position sensor 10, accelerator position sensor 12, throttle motor 13, vacuum sensor 15, oxygen concentration sensor 16, cold start injector 17, DC motor 20, an actuator of the variable valve timing mechanism 21, cam position sensor 22, crank position sensor 23, knock sensor 25, coolant temperature sensor 26, purge control valve 35, and intake air temperature sensor described above, as well as other actuators and sensors are connected to an electronic control unit (ECU) 37 that provides overall control for the engine 1. In the system shown in FIG. 1, there is provided an electronic control drive unit (EDU) 38 between the ECU 37 and the injector 5. The EDU 38 amplifies a driving current from the ECU 37 to generate a high voltage and large current required for driving the injector 5.

These actuators and sensors are controlled according to signals provided by the ECU 37 or send results of detection to the ECU 37. The ECU 37 is provided internally with a CPU that performs arithmetic operations, RAM that stores the results of arithmetic operations and various pieces of information, backup RAM that retains its memory by means of a battery, ROM that stores control programs, and other components. The ECU 37 controls the engine 1 based on various pieces of information including the intake passageway pressure and air-fuel ratio. Further, the ECU 37 performs arithmetic operations of the amount of fuel injected by the injector 5 and determines whether or not the oxygen concentration sensor 16 is fully operational.

Figure 2:
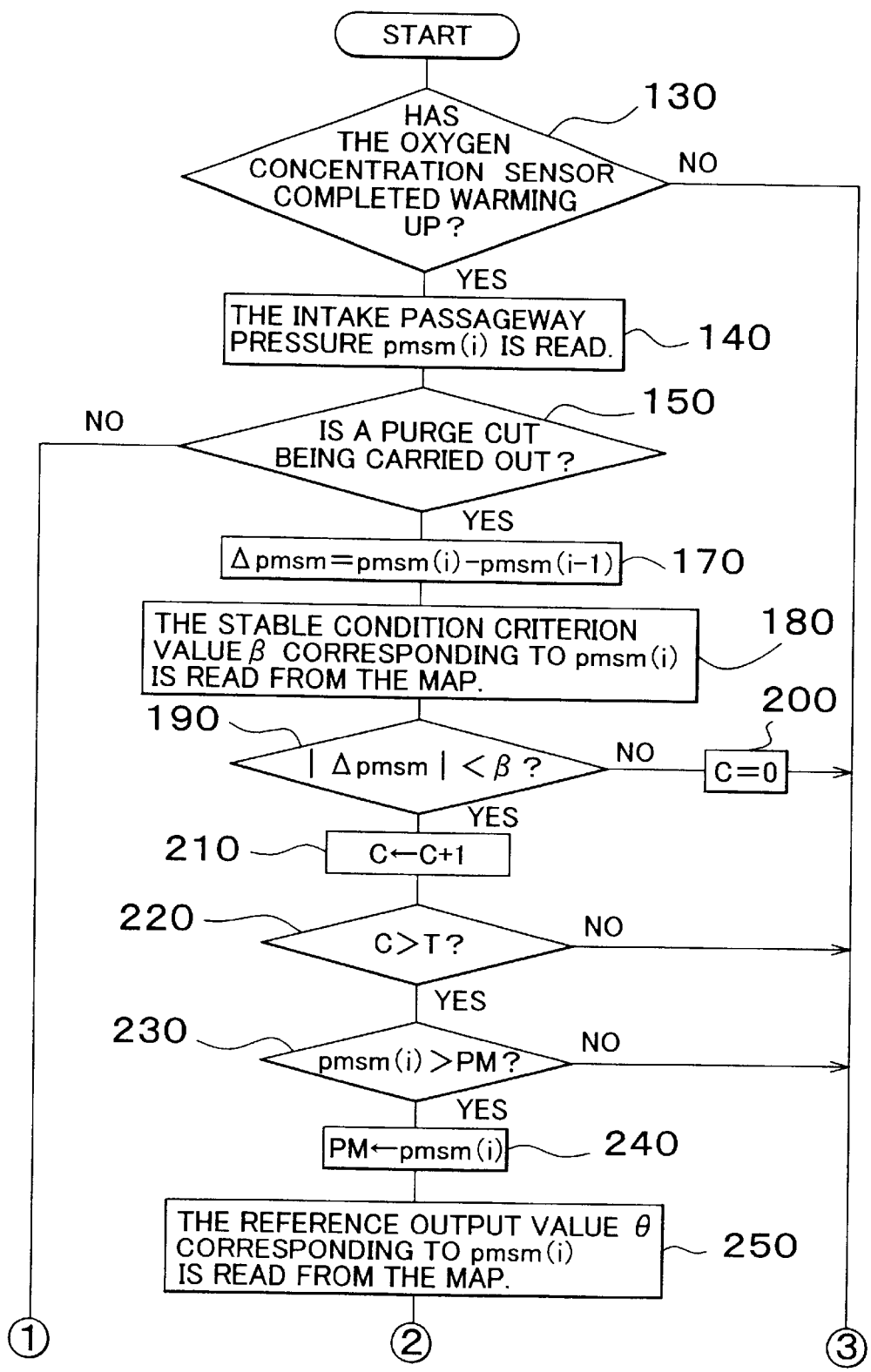
FIG. 2 is a flow chart (a first half portion) showing control provided to calibrate oxygen concentration sensor outputs through calculation of the calibration coefficient.
Figure 3:
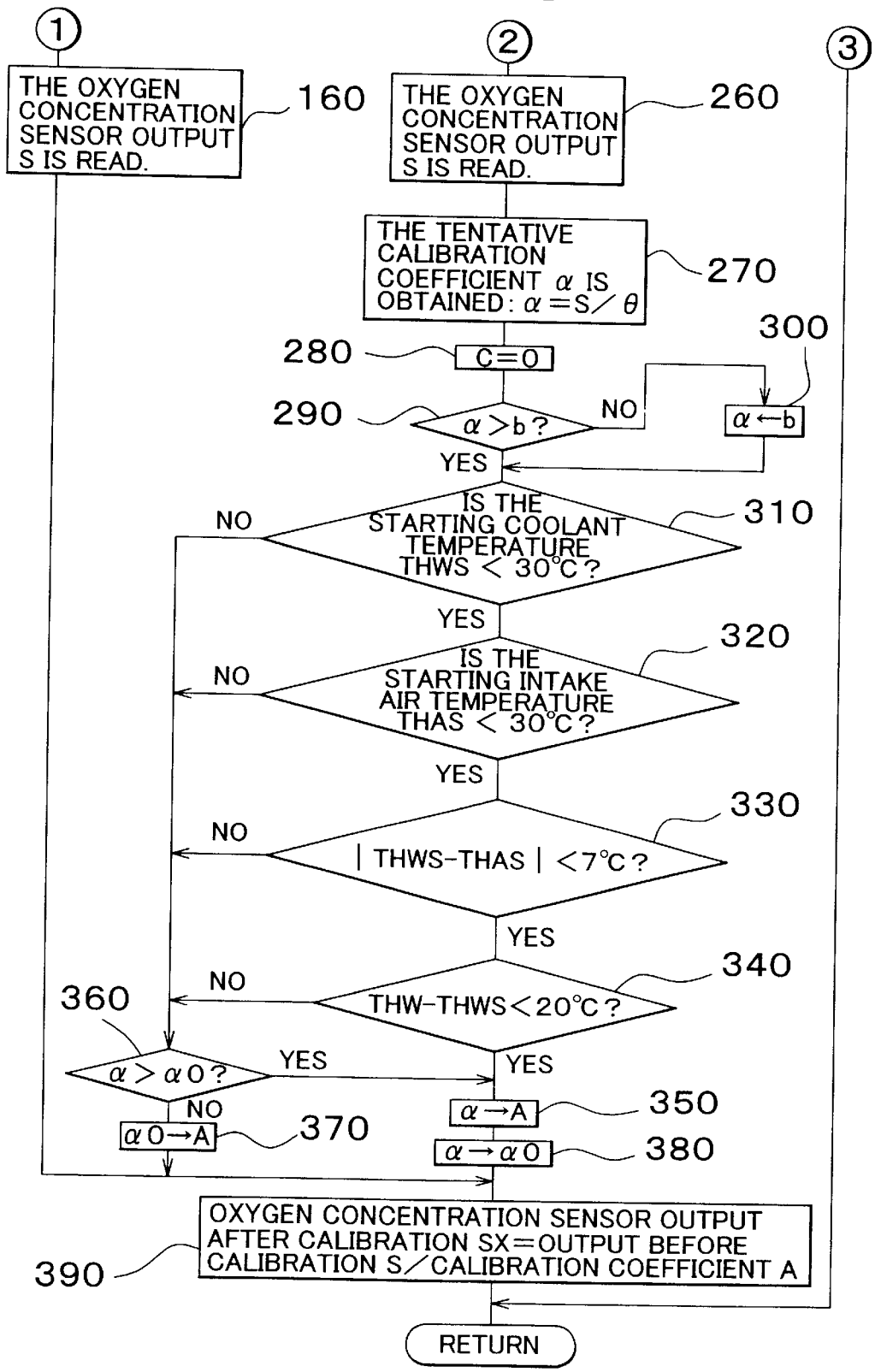
FIG. 3 is a flow chart (a second half portion) showing control provided to calibrate oxygen concentration sensor outputs through calculation of the calibration coefficient.
Figure 5:
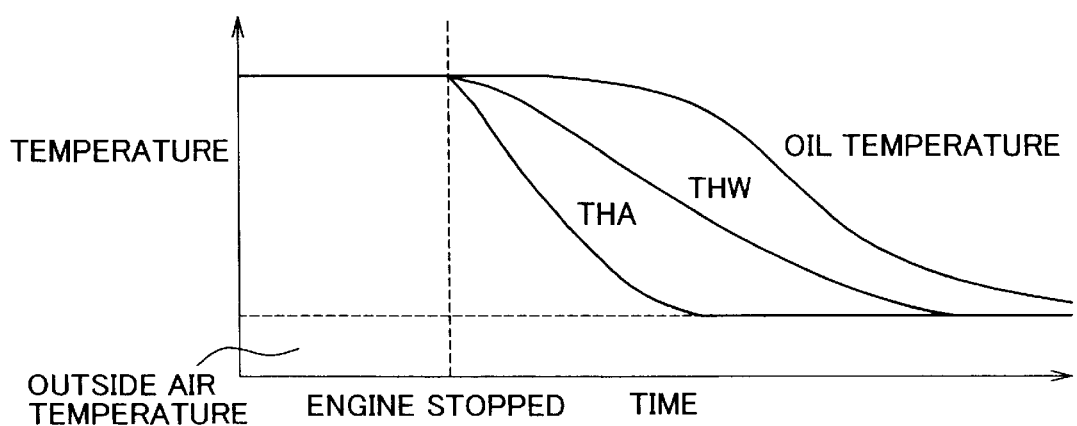
FIG. 5 is a chart showing general changes with time in intake air temperature THA, coolant temperature THW, and oil temperature after the engine has been stopped.

Next, calibration control provided for the oxygen concentration sensor 16 by using the calibration device according the present embodiment will be described. Flow charts of this control are shown in FIGS. 2, 3, and 5.

In the engine 1 according to the present embodiment, the oxygen concentration sensor 16 is provided in a prescribed arrangement along the intake passageway 4 and operations of the engine 1 are controlled (air-fuel ratio control and fuel injection amount control) based on concentration of oxygen contained in the intake air detected by the oxygen concentration sensor 16. This permits the engine 1 to be brought into an even more appropriate combustion condition, which results also in exhaust emission purification performance being enhanced.

One known method of operation control for the engine 1 is feedback control provided by detecting the exhaust air-fuel ratio of the exhaust gas (such control is also employed in the present embodiment). In such a control method, feedback control is provided according to the results obtained after combustion. Compared with this method, though, control in which oxygen concentration of intake air detected is incorporated into control of the engine 1 is superior in terms of an immediate effect on the engine operating conditions.

However, unless the output of the oxygen concentration sensor 16 is accurate, control of greater accuracy cannot be provided. Calibration is therefore performed so as to make the output of the oxygen concentration sensor accurate by providing calibration control to be described hereunder.

Referring to flow charts shown in FIGS. 2 and 3, control is executed at intervals of a predetermined period of time (e.g., for a predetermined number of revolutions of the engine 1 and for every several msec.). Using the flow charts shown in FIGS. 2 and 3, a calibration coefficient A used when calibrating the output of the oxygen concentration sensor 16 is obtained and the output is calibrated using this calibration coefficient.

First, it is determined whether or not the oxygen concentration sensor 16 has been warmed up (step 130). The oxygen concentration sensor 16 has a characteristic in which it is not able to yield stable detection results unless it has reached a predetermined temperature (activated temperature). In this step, it is determined whether the oxygen concentration sensor 16 has reached this activated temperature (namely, whether it has completed warming up). Electric power or the like may at times be employed to forcibly raise the temperature so that the oxygen concentration sensor 16 is activated at an early stage.

If at step 130 it is determined that the oxygen concentration sensor 16 has not warmed up, the output of the oxygen concentration sensor 16 contains a large number of errors, making it impossible to perform calibration or calculate the calibration coefficient A. The control shown in this flow chart is then temporarily terminated. Under such conditions, the output of the oxygen concentration sensor 16 is not used for any other type of control. If on the other hand, at step 130 it is determined that the oxygen concentration sensor has warmed up, the intake passageway pressure pmsm(i) detected by the vacuum sensor 15 at step 140.

It is then determined whether or not purge control that purges fuel vapors in the fuel tank to the intake passageway 4 is being carried out (or in the process of a purge cut) (step 150). If step 150 is affirmed, namely, if a purge cut is being carried out, the following steps will be executed to calculate the calibration coefficient A.

In the steps to be described hereunder, the oxygen concentration sensor 16 is calibrated using the intake passageway pressure pmsm detected by the vacuum sensor 15 and other data. If trapped fuel is being purged to the intake passageway, however, it is impossible to accurately estimate oxygen concentration in the intake air based on the intake passageway pressure pmsm. If the air does not contain purged fuel, it is possible to estimate oxygen concentration from the amount of intake air by way of the intake passageway pressure pmsm; however, if trapped fuel is purged, it causes oxygen concentration to fluctuate. In step 150, therefore, it is determined whether or not a purge cut is being carried out and the calibration coefficient A is calculated only if it is determined that a purge cut is being carried out.

If step 150 is affirmed, namely, if purging of trapped fuel is not being carried out, the difference between the intake passageway pressure pmsm(i) detected by the vacuum sensor 15 at that particular point in time and the intake passageway pressure detected last pmsm(i-1) is calculated to find a fluctuation range Δpmsm (step 170). A stable condition criterion value β corresponding to the intake passageway pressure pmsm(i) at that particular point in time is then read from a map (step 180) to determine whether or not the absolute value of the fluctuation range Δpmsm obtained through calculation is smaller than the stable condition criterion value β (step 190). If the fluctuation range Δpmsm is smaller, it means that there is only a small fluctuation in the intake passageway pressure pmsm. The stable condition criterion value β is a variable value set such that it can be determined that the intake passageway pressure pmsm fluctuates little (is stable).

Figure 4:
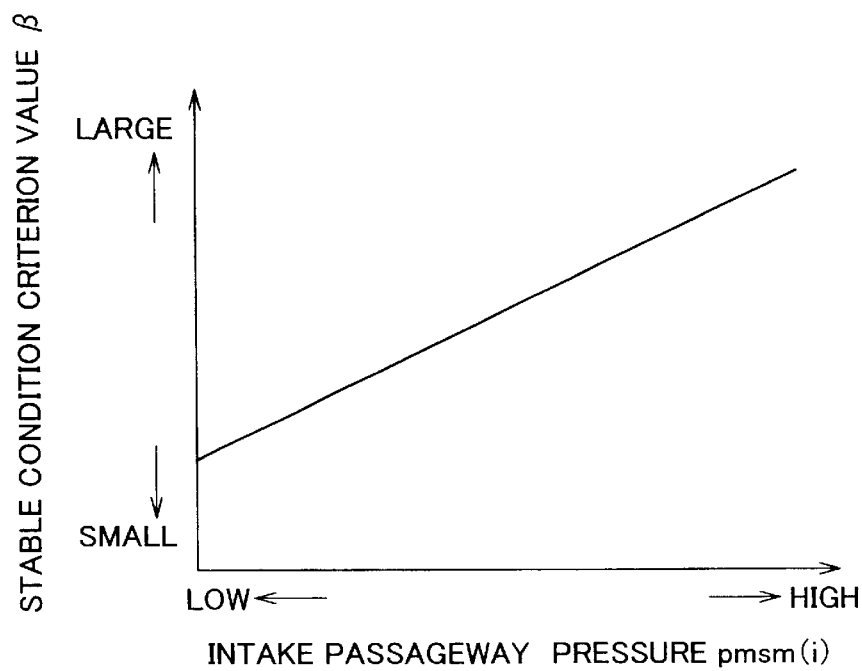
FIG. 4 is a map showing the relationship between the intake passageway pressure and the stable condition criterion value.

The higher the intake passageway pressure pmsm detected (in this case, the intake passageway pressure pmsm (i) detected at that particular point in time), the larger the stable condition criterion value β is set, and the lower the intake passageway pressure pmsm detected, the smaller the stable condition criterion value β is set. A map representing the relationship between the intake passageway pressure pmsm and the stable condition criterion value β is shown in FIG. 4. The response of the oxygen concentration sensor 16 is generally slower than that of the pressure sensor (vacuum sensor 15) and the output thereof is linear with respect to pressure. As a result, in a region in which the intake passageway pressure pmsm remains low, the output from the oxygen concentration sensor 16 is small and the percentage that errors arising from a response lag and the like occupy in the total output of the oxygen concentration sensor 16 increases. Namely, the detection accuracy of the oxygen concentration sensor 16 (output accuracy) deteriorates the smaller the intake passageway pressure pmsm.

In the region in which the intake passageway pressure pmsm remains low, the above stable condition criterion value β is set to a small value, thereby narrowing the fluctuation range Δpmsm over which the intake passageway pressure pmsm can be determined as being stable. This allows the calculation of the calibration coefficient A made based on the output of the oxygen concentration sensor 16 to be less susceptible to effects of errors arising from a response lag of the oxygen concentration sensor 16 and the like.

In a region in which the intake passageway pressure pmsm is high, on the other hand, the above stable condition criterion value β is set to a large value, thereby widening the fluctuation range Δpmsm over which the intake passageway pressure pmsm can be determined to be stable. That is, the fluctuation range Δpmsm over which the intake passageway pressure pmsm can be determined to be stable is widened by setting the stable condition criterion value β to a large value. Even with such a setting made, the percentage that errors arising from a response lag and the like occupy in the total output of the oxygen concentration sensor 16 remains small and the calculation of the calibration coefficient A remains less susceptible to effects of errors arising from a response lag of the oxygen concentration sensor 16 and the like.

Step 210 and step 220 are next used to determine whether or not a condition detected by the step 190 is maintained for a predetermined period of time. First, if at step 190 it is determined that the intake passageway pressure pmsm at that particular point in time is stable, a counter C (initial value is 0) is counted up by one (step 210). If at step 190 it is determined that the intake passageway pressure pmsm is not stable, the counter C is reset to the initial value of 0 (step 200) and the control shown in FIG. 2 and FIG. 3 is temporarily terminated.

Subsequently to step 210, it is determined whether the counter C value is larger than a predetermined value T (step 220). If the counter C value is larger than the predetermined value T, it can be determined that the intake passageway pressure pmsm remains stable for a predetermined period of time. When the intake passageway pressure pmsm remains stable for a predetermined period of time as a result of the control shown in FIG. 2 and FIG. 3 being repeatedly executed, the counter C is kept counting up until it is determined at step 220 that the predetermined period of time has elapsed. If the intake passageway pressure pmsm remains stable but the period of time through which the intake passageway pressure pmsm remains stable does not reach the predetermined period of time, the control shown in FIG. 2 and FIG. 3 is temporarily suspended at step 220, with the counter C value not being reset, and the steps are repeated beginning with step 130 onward. If at step 190 it is determined that the intake passageway pressure pmsm has become unstable while steps are being repeated, the counter C is reset to the initial value of 0.

If at step 220 it is determined that the predetermined period of time has elapsed, it is determined whether the intake passageway pressure pmsm(i) is higher than the intake passageway pressure PM upon the last update for the calibration coefficient A stored in memory (step 230). If at step 230 it is determined that, the intake passageway pressure pmsm(i) at that particular point in time is lower than the intake passageway pressure PM developing when the calibration coefficient A is updated last, the control shown in FIG. 2 and FIG. 3 is temporarily terminated without newly calculating and updating the calibration coefficient A.

The following notes the reason why the control is terminated without updating the calibration coefficient A when it is determined at step 230 that the intake passageway pressure pmsm(i) at that particular point in time is lower than the intake passageway pressure PM when the calibration coefficient A was updated last.

That is, the percentage occupied by the errors contained in the output of the oxygen concentration sensor 16, including those arising from the response lag mentioned earlier, in the entire output becomes small when the output is large. Moreover, the oxygen concentration sensor 16 has a characteristic, as noted earlier, that the higher the pressure at detection, the greater the output thereof, even if the oxygen concentration remains unchanged. It can therefore be safe to consider that the region in which the output of the oxygen concentration sensor 16 is large, namely, the calibration coefficient A calculated with the intake passageway pressure, offers greater accuracy. In this control, therefore, the calibration coefficient A is not updated and the last calibration coefficient A, which is considered to offer a greater accuracy, is kept as is if the intake passageway pressure pmsm(i) is lower than when the calibration coefficient A was updated last.

If at step 230 it is determined that the intake passageway pressure pmsm(i) at that particular point in time is higher than the intake passageway pressure PM developing when the calibration coefficient A was updated last, the intake passageway pressure pmsm(i) at that particular point in time is stored in backup RAM of the ECU 37 as the intake passageway pressure (upon last update) PM before the calibration coefficient A is newly updated for the next determination (step 240). The calibration coefficient A is then actually updated as detailed in the following. First, an output reference value θ corresponding to the detected intake passageway pressure pmsm(i) is read from the map (step 250). An output S of the oxygen concentration sensor 16 is then read (step 260).

The output reference value θ is an output value provided when an oxygen concentration sensor 16 of medium tolerance detects ordinary air not containing unburned fuel. Namely, the output reference value θ may be considered as a reference value not containing the variations of each oxygen concentration sensor 16. The map used to find the output reference value θ is prepared in advance by using an oxygen concentration sensor 16 of medium tolerance not deteriorated with age. This map is a two-dimensional map showing the relationship between the intake passageway pressure pmsm and the output reference value θ. It is quite common to estimate (calculate) the amount of intake air from the intake passageway pressure pmsm and it is possible to obtain the oxygen concentration based on the ratio of the estimated amount of intake air and the oxygen in the air.

A tentative calibration coefficient α is next obtained using the following equation (step 270): (tentative calibration coefficient α)=(detected output S of the oxygen concentration sensor 16)/(output reference value θ obtained by the map); wherein the tentative calibration coefficient α is 1 if the oxygen concentration sensor 16 has the same performance as that having medium tolerance.

After step 270, the value of the counter C is reset to the initial value of 0 for the next updating of the calibration coefficient A (step 280). Furthermore, it is then determined whether the tentative calibration coefficient α obtained through calculation is larger than a predetermined lower limit guard value b (step 290). If at step 290 it is determined that the tentative calibration coefficient α obtained through calculation is equal to or less than the predetermined lower limit guard value b, the tentative calibration coefficient α is replaced by the lower limit guard value b (step 300). If at step 290 it is determined that the tentative calibration coefficient α is greater than the predetermined lower limit guard value b, it is maintained as it is.

If the tentative calibration coefficient α is small, the following reason could contribute to it, namely, a substance of some type is mixed with the intake air for some reason even though a purge cut is being carried out, thus lowering the oxygen concentration, which makes the actual output of the oxygen concentration sensor 16 small. A good case in point is when the amount of unburned fuel contained in blow-by gas becomes inordinately large during a purge cut and is recirculated to the intake passageway 4. Nonetheless, it is also possible that the tentative calibration coefficient α is not calculated accurately. If the output of the oxygen concentration sensor 16 is calibrated using an inaccurate tentative calibration coefficient α, it stands to reason that the results of such calibration would be inaccurate.

If the tentative calibration coefficient α is smaller than a predetermined value, namely, the lower limit guard value b, then the tentative calibration coefficient α is replaced by this lower limit guard value b, thereby reducing the effect that there would be when the tentative calibration coefficient α obtained through calculation is not accurate. It is nonetheless possible that the tentative calibration coefficient α obtained through calculation is accurate, though smaller than the lower limit guard value b. The tentative calibration coefficient α obtained through calculation is also replaced by the lower limit guard value b in such a case; however, the output of the oxygen concentration sensor 16 for the lower limit guard value b can be calibrated. In this case, indeed the lower limit guard value b detracts from the benefits of calibration, but, considering the case in which adverse effects are brought about by an inaccurate tentative calibration coefficient α obtained through calculation, overall calibration control of the output of the oxygen concentration sensor 16 is more stable.

In the subsequent steps from step 310 through step 340, it is determined whether the engine 1, which has been cold-started, has completed warming up or not. This is because the effects of blow-by gas change depending on whether the cold-started engine has completed warming up or not. Thereafter, the tentative calibration coefficient α is determined as the final calibration coefficient A in consideration of the effects of blow-by gas. As described earlier, the blow-by gas containing unburned fuel can at times be recirculated to the upstream side of the throttle valve of the intake passageway 4.

However, in a condition immediately after a cold engine has been started, in which the engine has not yet completely warmed up, the amount of intake air itself is large and therefore the concentration of unburned fuel contained in the blow-by gas (equivalent to the drop in oxygen concentration) is so small that it is negligible. It can therefore be determined that, in the condition in which the cold-started engine has not yet completely warmed up immediately after it has been started, the tentative calibration coefficient α calculated this time is an accurate value not affected by unburned fuel contained in the blow-by gas. Thus, the calibration coefficient A is determined (step 350, after step 340 has been affirmed).

On the other hand, in a condition immediately after a warm engine has been started, or in which an engine, whether it has been started in a cold or warm state, has already completed warming up, there is less intake air than there is immediately after a cold engine has been started and the final calibration coefficient A is determined in consideration of the concentration of unburned fuel contained in the blow-by gas (equivalent to the drop in oxygen concentration). To be more specific, if the tentative calibration coefficient α calculated this time is greater than a value stored in memory α0, which is the tentative calibration coefficient α calculated previously, it is determined that the calibration coefficient α calculated previously (=previous value α0) was affected by blow-by gas and the oxygen concentration was calculated low, and the tentative calibration coefficient α calculated this time is more accurate. Then, the tentative calibration coefficient α calculated this time is taken to update the final calibration coefficient A (step 350, after step 360 has been affirmed).

If the tentative calibration coefficient α calculated this time is smaller than the value stored in memory α0, on the other hand, it is determined that the tentative calibration coefficient α calculated this time is affected by blow-by gas and the oxygen concentration is being calculated low, and the calibration coefficient α calculated previously (=stored value α0) is more accurate. The tentative calibration coefficient α calculated this time is therefore abandoned and the stored value α0 is taken to update the final calibration coefficient A (step 370, after step 360 has been negated). If the final calibration coefficient A is updated with the tentative calibration coefficient α calculated this time, the tentative calibration coefficient α calculated this time is stored in memory as the stored value α0 for use when updating the calibration coefficient A next time (step 380).

The reason why the tentative calibration coefficient α calculated this time is taken to update the final calibration coefficient A only when the tentative calibration coefficient α calculated this time is greater than the stored value α0 in a case not immediately after a cold start or when the engine has completely warmed up is described in detail once more below.

The fact that the tentative calibration coefficient α calculated this time is greater than the calibration coefficient α calculated last time (=stored value α0) means that the output S of the oxygen concentration sensor 16 becomes greater than the output reference value θ. This provides good reason to believe that the intake air this time contains a higher oxygen concentration than the last time, that is, the intake air this time is leaner than the last time, not affected by unburned fuel contained in the blow-by gas. In such cases, it is safe to conclude that the current calculation is more accurate than the last one, not being affected by unburned fuel contained in the blow-by gas, and the tentative calibration coefficient α calculated this time is taken for updating as the final calibration coefficient A (step 350, after it is determined at step 360 that is not greater than 0.

The fact that the tentative calibration coefficient α calculated this time is smaller than the tentative calibration coefficient α calculated last time (=stored value α0) means, on the other hand, that the output S of the oxygen concentration sensor 16 becomes smaller than the output reference value θ. This provides good reason to believe that the intake air this time contains a lower oxygen concentration than the last time, that is, the intake air this time is richer than the last time, being affected by unburned fuel contained in the blow-by gas. In such cases, it can be concluded that the last calculation was more accurate than the current one, not being affected by unburned fuel contained in the blow-by gas, and the tentative calibration coefficient α calculated last time is taken for updating as the final calibration coefficient A (step 370, after it is determined at step 360 that is greater than 0.

Detailed descriptions of each of step 310 through step 380 will be given in below. First, it is determined whether the engine 1 is started from a cold state or not by determining whether a starting coolant temperature THWS stored when the engine 1 is started is less than 30° C. or not (step 310) and whether a starting intake air temperature THAS stored when the engine 1 is started is less than 30° C. or not (step 320). If both step 310 and step 320 hold true, then it is considered that the engine is started from a cold state.

It is then determined whether the absolute value of a difference between the starting coolant temperature THWS and the starting intake air temperature THAS is less than 7° C. or not (step 330). In step 330, it is determined whether or not the engine has been left to stand idle for a long period of time before it was started. FIG. 5 shows general changes with time in the coolant temperature THW, intake air temperature THA, and a lubricating oil temperature after the engine 1 has been stopped. As is evident from FIG. 5, the intake air temperature THA becomes equal to the outside air temperature earlier than do the coolant temperature THW and the lubricating oil temperature after the engine 1 has been stopped. Further, the lubricating oil temperature takes longer to decrease than the coolant temperature THW and the intake air temperature THA.

If the absolute value of the difference between the starting coolant temperature THWS and the starting intake air temperature THAS is less than a predetermine value (in this case 7° C.), it can then be determined that the engine 1 has been left to stand idle for a long period of time. The absolute value of the difference between the starting coolant temperature THWS and the starting intake air temperature THAS can also be less than 7° C. when the engine 1 is restarted (started in a warm state) immediately after it has been stopped. Such a case is, however, excluded by step 310 or step 320 and, if at step 330 it is determined that the temperature difference is less than 7° C., it can be determined that the engine has been left to stand idle for a long period of time.

It is then determined whether the difference between the current coolant temperature THW and the starting coolant temperature THWS is less than 20° C. or not (step 340). If the difference between the current coolant temperature THW and the starting coolant temperature THWS is less than a predetermined value (in this case set to 20° C.), it can be determined that the coolant temperature has not yet risen sufficiently after the engine 1 has been started, namely, the engine has not yet completely warmed up. If all of the conditions from step 310 through step 340 are met, it can be determined that the engine has not yet completely warmed up immediately after being started in a cold state. Thus, the tentative calibration coefficient α calculated this time is set and stored in memory as the final calibration coefficient A (step 350).

If any one of the conditions from step 310 to step 340 is not met, on the other hand, it indicates that the engine has not yet completely warmed up immediately after being started from a cold state so consideration is given to the effect of blow-by gas. To be more specific, if the tentative calibration coefficient α calculated this time is greater than the tentative calibration coefficient α calculated last time (=stored value α0), it can be determined that an accurate tentative calibration coefficient α can be found through calculation, being subjected to less of an effect from blow-by gas than the last time. It is therefore determined whether the tentative calibration coefficient α calculated this time is greater than the stored value α0 (step 360) and, if the condition of step 360 is met, then the tentative calibration coefficient α calculated this time is set and stored in memory as the final calibration coefficient A (step 350).

If the final calibration coefficient A is updated using the tentative calibration coefficient α calculated this time, this tentative calibration coefficient α calculated this time is saved in backup RAM of the ECU 37 as the stored value α0 to be used for the next updating of the calibration coefficient A (step 380). If the condition of step 360 is not met, on the other hand, the tentative calibration coefficient α calculated last time (=stored value α0) is considered to be more accurate, not being affected by the blow-by gas, and the stored value α0 is set and stored in memory as the final calibration coefficient A (step 370).

The output S of the oxygen concentration sensor 16 is next actually calibrated using the established calibration coefficient A. Assuming that the output of the oxygen concentration sensor 16 after calibration is Sx, then the following equation holds true. That is, (oxygen concentration sensor 16 output after calibration Sx)=(output before calibration S)/(calibration coefficient A) (step 390). The output of the oxygen concentration sensor 16, which has undergone calibration, is used for air-fuel ratio control and fuel injection amount control of the engine 1.

Calculation of the calibration coefficient A during a purge cut has so far been described. If the condition of step 150 is not met, namely, if trapped fuel is purged to the intake passageway 4, the output S of the oxygen concentration sensor 16 is read (step 160) and thereafter the output of the oxygen concentration sensor 16 is calibrated in step 390 in the same manner based on Sx=S/A. The calibration coefficient A used at this time is the latest as of that particular point in time.

The calibration method applicable to the oxygen concentration sensor 16 described heretofore may be one that uses various types of information available from the intake side. In the present embodiment, however, further calibration is carried out by using the various types of information available from the exhaust side to even further enhance calibration accuracy. To be more specific, the air-fuel ratio sensor 28 provided in a prescribe arrangement along the exhaust passageway 7 is used to correct the calibration coefficient A set with the flow charts shown in FIG. 2 and FIG. 3. The flow chart for this control is shown in FIG. 6.

The control depicted in FIG. 2 and FIG. 3 is executed during a purge cut of trapped fuel to calculate the calibration coefficient A. Meanwhile, the control shown in FIG. 6 corrects the calibration coefficient A during an exhaust cycle of purging of trapped fuel. The control shown in FIG. 6 is stored as a program in ROM of the ECU 37, repeatedly executed for a predetermined period of time (for a predetermined number of revolutions of the engine 1 and for every several msec.).

First, it is determined whether or not purging of trapped fuel is being carried out (step 400). While purging is being carried out, the output of the oxygen concentration sensor 16 is calibrated with the set calibration coefficient A and fuel injection control (air-fuel ratio control) and other controls are executed based on this calibrated output. Calibration accuracy is even more enhanced by further correcting the calibration coefficient A based on the results of control using the set calibration coefficient A.

Figure 6:
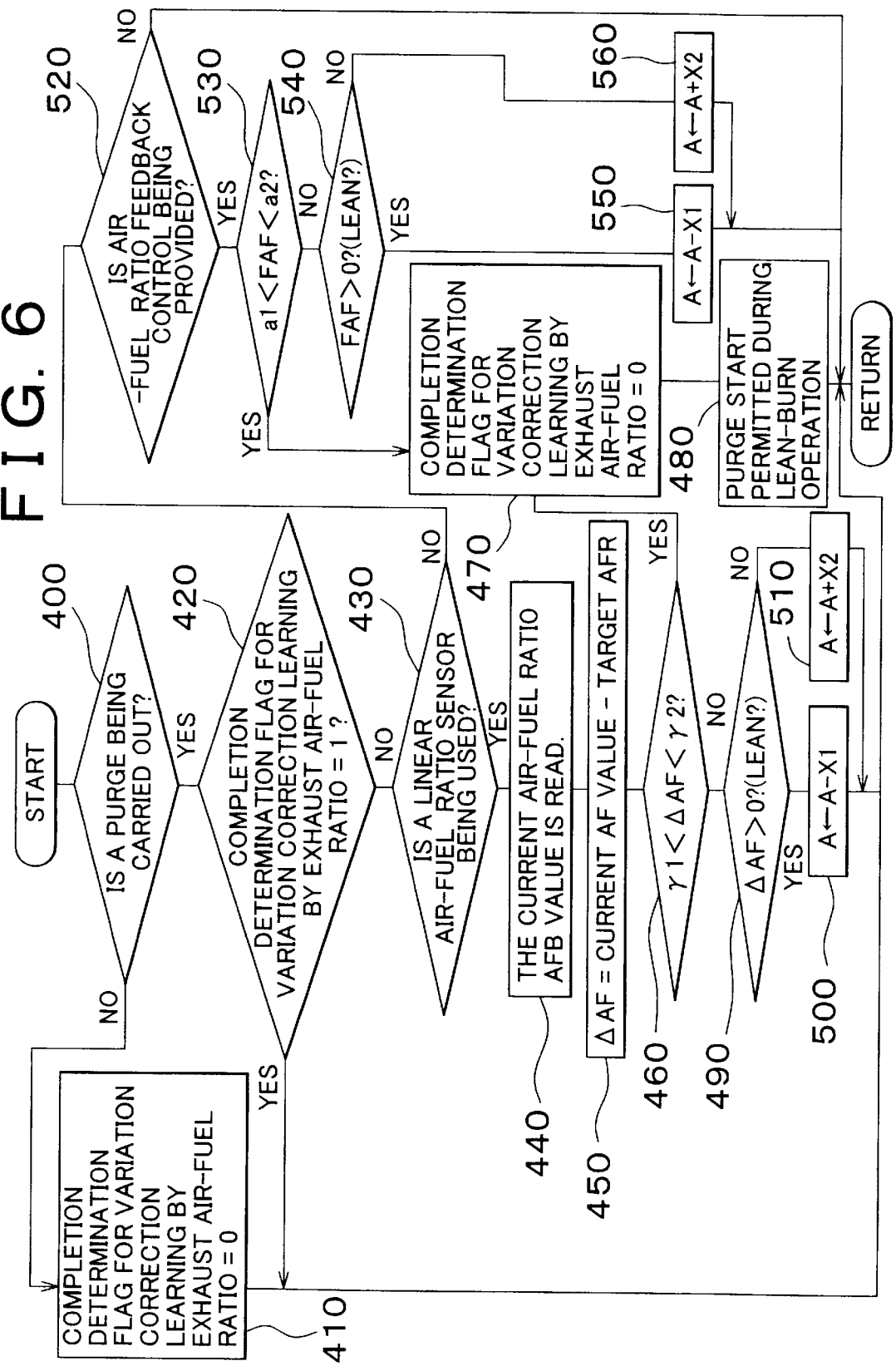
FIG. 6 is a flow chart showing control provided for correcting the calibration coefficient based on the output provided by an air-fuel ratio sensor.

If at step 400 purging of trapped fuel to the intake passageway 4 is not being executed, a correction of the calibration coefficient A by this control (variation correction learning by the exhaust air-fuel ratio) is not made, a completion determination flag for variation correction learning is set to 0 (step 410), and the control shown in FIG. 6 is temporarily terminated. If the condition of step 400 is met, on the other hand, namely, if purging of trapped fuel to the intake passageway 4 is being executed, it is determined whether the completion determination flag for variation correction learning mentioned earlier is 1 or not (step 420). The case in which the completion determination flag for variation correction learning is set to 1 will be detailed later. The completion determination flag for variation correction learning is set to 1 when it is not necessary to correct the calibration coefficient A judging from the detected exhaust air-fuel ratio.

If the condition of step 420 is met, this control has already been executed at least once and the completion determination flag for variation correction learning is set to 1. Therefore there is then no need to correct the calibration coefficient A and the control shown in FIG. 6 is temporarily terminated. If a purge cut of trapped fuel has been made, however, the completion determination flag for variation correction learning can be set from 1 to 0 again in step 400 during the course of repeated execution of the control shown in FIG. 6. In such a case, the condition of step 420 is not met, even with a history in which the completion determination flag for variation correction learning has been set to 1.

If the condition of step 420 is not met, it is determined whether or not a linear air-fuel ratio sensor is used for the air-fuel ratio sensor 28 (step 430). As described earlier, a linear air-fuel ratio sensor that is capable of linearly detecting the exhaust air-fuel ratio covering from a rich zone to a lean zone or an oxygen sensor that is activated or deactivated to determine when the exhaust air-fuel ratio is in a rich zone or a lean zone is used as the air-fuel ratio sensor 28. In step 430 it is determined which one of these two is used.

The control shown in FIG. 6 is stored in ROM of the ECU 37 as a program. This program has been prepared so as to be applicable to either of these types used as the air-fuel ratio sensor 28. In the actual process executed, therefore, the specific type used as the air-fuel ratio sensor 28 is identified in step 430 and, in the subsequent steps, control is provided according to the respective type of air-fuel ratio sensor.

A case will be first described in which the condition of step 430 is met, namely, a linear air-fuel ratio sensor is used as the air-fuel ratio sensor 28. In this case, the air-fuel ratio sensor 28 is used to read the current exhaust air-fuel ratio AF (step 440). If a plurality of air-fuel ratio sensors 28 are used, a representative sensor may be selected based on the ignition timing, or an average value of the readings taken by a plurality of sensors may be taken. A difference $\Delta$AF between the detected exhaust air-fuel ratio AF and a target air-fuel ratio AF, or a control target, is then calculated (step 450). It is then determined whether this difference $\Delta$AF falls within a predetermined range ($\gamma 1 < \Delta AF < \gamma 2$) (step 460); where, $\gamma 1 < 0$ and $0 < \gamma 2$.

If the condition step 460 is met, it means that the output of the oxygen concentration sensor 16 is properly calibrated and a target exhaust air-fuel ratio is obtained. The completion determination flag for variation correction learning is then set to 1 without correcting the calibration coefficient A (step 470). Then, a purge of trapped fuel during lean-burn operation is permitted (step 480). A purge during lean-burn operation is permitted only through this step 480. If condition of step 400 of the control shown in FIG. 6 is met, the engine 1 is considered to be running in a stoichiometric zone or a rich zone.

The engine 1 according to the present embodiment is the type of cylinder injection of fuel capable of burning a lean mixture as described earlier. The air-fuel ratio during a lean burn approaches the maximum as high as 50, which makes the accuracy in detecting oxygen concentration of the intake air highly critical. The control shown in FIG. 6 therefore does not permit a purge particularly during lean-burn operation until conditions develop in which the completion determination flag for variation correction learning is set to 1 in consideration of the fact that the output of the oxygen concentration sensor 16 does not enable accurate detection. Accuracy is required of the output of the oxygen concentration sensor 16 even while the engine 1 is running in a stoichiometric zone or a rich zone; an even higher accuracy is required when the engine is running in a lean zone.

If the condition step 460 is not met, on the other hand, it indicates that there is a wide difference between the detected exhaust air-fuel ratio AF and the target air-fuel ratio AFr and that the output of the oxygen concentration sensor 16 is not necessarily being properly calibrated. In this case, it is first determined whether the difference $\Delta$AF is positive or not, namely, whether or not the detected exhaust air-fuel ratio AF is on the lean side with respect to the target air-fuel ratio AFr (step 490).

If the condition of step 490 is met, namely, the detected exhaust air-fuel ratio AF is on a leaner side than the target air-fuel ratio AFr, the calibration coefficient A is corrected so that the output of the oxygen concentration sensor 16 will be richer than the current level. Correcting the calibration coefficient A so as to make the output of the oxygen concentration sensor 16 on the rich side (on the low side in terms of oxygen concentration) means to make the output of the oxygen concentration sensor smaller. In this case, the correction is made so as to make the calibration coefficient A smaller, wherein the calibration coefficient A is decreased by only a predetermined value of X1 and set as a new calibration coefficient A (step 500).

If the condition of step 490 is not met, namely, if the detected exhaust air-fuel ratio AF is richer than the target air-fuel ratio AFr, on the other hand, the calibration coefficient A is corrected so that the output of the oxygen concentration sensor 16 will be leaner than the current level. Correcting the calibration coefficient A so as to make the output of the oxygen concentration sensor 16 on the lean side (on the high side in terms of oxygen concentration) means to make the output of the oxygen concentration sensor greater. In this case, the correction is made so as to make the calibration coefficient A greater, wherein the calibration coefficient A is increased by only a predetermined value of X2 and set as a new calibration coefficient A (step 510).

The above description is based on the case in which a linear air-fuel ratio sensor is employed as the air-fuel ratio sensor. The description to be given hereunder is based on a case in which an oxygen sensor is used as the air-fuel ratio sensor, namely, the case in which the condition step 430 is not met. Since the output of the air-fuel ratio sensor 28 is binary, either ON or OFF, in this case, it is not possible to determine by using the output of the air-fuel ratio sensor 28 how much the current exhaust air-fuel ratio AF deviates from the target air-fuel ratio AFr. An air-fuel ratio feedback correction coefficient FAF in air-fuel ratio feedback control is therefore employed in this case.

To correct the calibration coefficient A by using the air-fuel ratio feedback correction coefficient FAF, accurate correction is ensured only when the air-fuel ratio feedback correction coefficient FAF is being calculated and updated. If the condition of step 430 is not met, therefore, it is first determined whether or not the air-fuel ratio feedback control is being executed (step 520). If the condition of step 520 is not met, no correction of the calibration coefficient A can be made and the control shown in FIG. 6 is temporarily terminated. If step 520 is affirmed, it is evaluated whether or not the air-fuel ratio feedback correction coefficient FAF falls within a predetermined range (a1<FAF<a2) (step 530); where, a1<0 and 0<b2. The value of the air-fuel ratio feedback correction coefficient FAF is maintained at around 0 in a generally targeted stoichiometric zone.

If the condition of step 530 is met, therefore, it is determined that the output of the oxygen concentration sensor 16 is properly calibrated and a target exhaust air-fuel ratio is obtained. The completion determination flag for variation correction learning is then set to 1 without correcting the calibration coefficient A (step 470) and a purge of trapped fuel during lean-burn operation is permitted (step 480). If the condition of step 530 is not met, on the other hand, it is determined that the output of the oxygen concentration sensor 16 is not necessarily calibrated correctly. In this case, it is determined whether or not the air-fuel ratio feedback correction coefficient FAF is positive (step 540). If the air-fuel ratio feedback correction coefficient FAF is positive, it indicates that the exhaust air-fuel ratio is on the lean side. The air-fuel ratio feedback correction coefficient FAF becomes positive as the exhaust air-fuel ratio on the lean side is gradually shifted toward the rich side.

If condition of step 540 is met, namely, if the output of the air-fuel ratio sensor 28 indicates that the exhaust air-fuel ratio A/F is leaner than the target stoichiometric zone, then it can be considered that the output of the oxygen concentration sensor 16 results in a mixture on the lean side and thus the calibration coefficient A is corrected so that the output becomes richer than the current level. Correcting so that the output of the oxygen concentration sensor 16 results in a mixture on the rich side (with a lower concentration of oxygen) means that the output is made smaller, which results in the calibration coefficient A being made smaller. In this case, the calibration coefficient A is decreased by only a predetermined value of X1 and set as a new calibration coefficient A (step 550).

If the condition of step 530 is not met, namely, if the output of the air-fuel ratio sensor 28 indicates that the exhaust air-fuel ratio A/F is richer than the target stoichiometric zone, on the other hand, it can be considered that the output of the oxygen concentration sensor 16 results in a mixture on the rich side and thus the calibration coefficient A is corrected so that the output becomes leaner than the current level. Correcting so that the output of the oxygen concentration sensor 16 results in a mixture on the lean side (with a higher concentration of oxygen) means that the output is made greater, which results in the calibration coefficient A being made greater. In this case, the calibration coefficient A is increased by only a predetermined value of X2 and set as a new calibration coefficient A (step 560).

Figure 7:
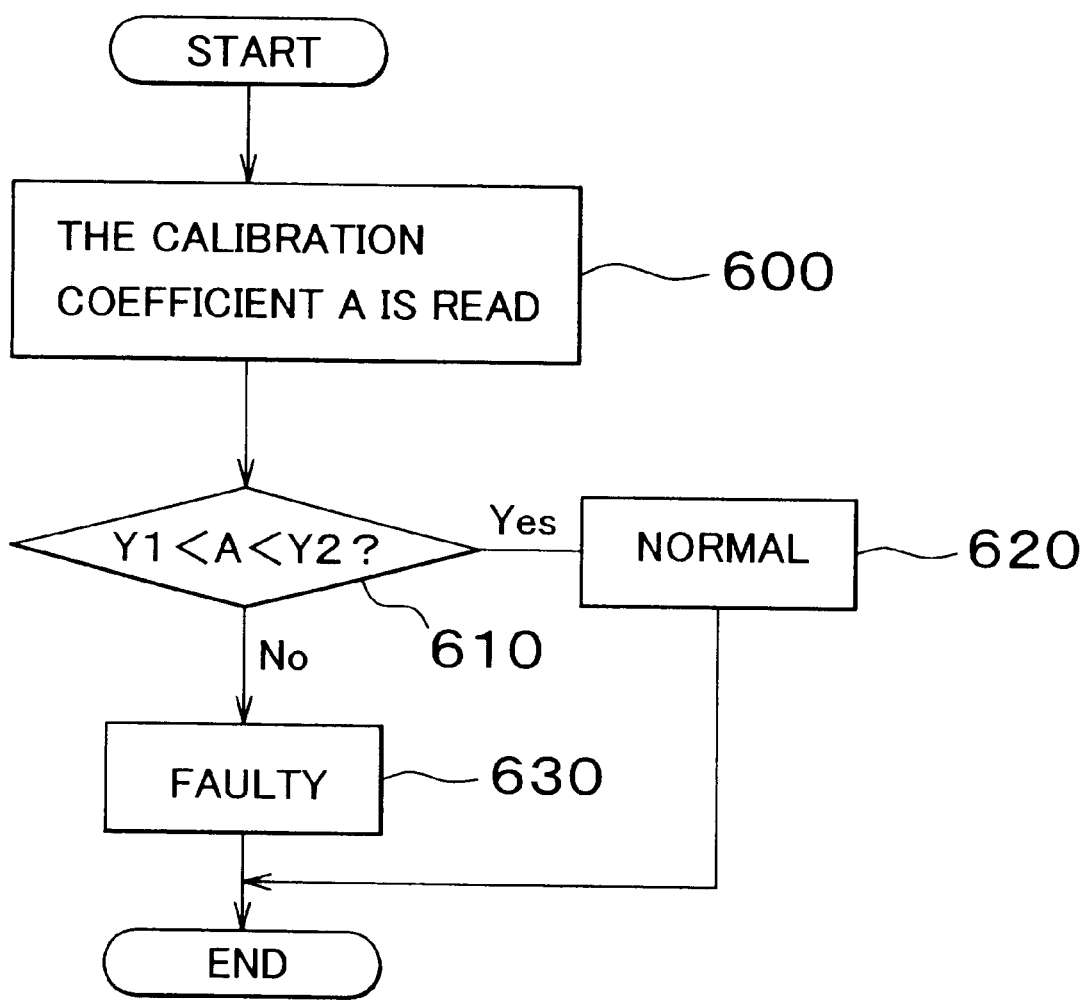
FIG. 7 is a flow chart showing control provided for determining if the oxygen concentration sensor is faulty.

The calibration device according to the present embodiment not only calibrates the output of the oxygen concentration sensor 16, but detects a fault, as well. FIG. 7 shows the flow chart for this control. The fault diagnostics routine first reads the calibration coefficient A set and stored in memory shown in FIG. 2 and FIG. 3 (step 600). The tentative calibration coefficient α or the stored value α0 may be used, instead. It is then determined whether or not this calibration coefficient A falls within a predetermined range (Y1<A<Y2) (step 610).

As described earlier, any deviation of the actual output of the oxygen concentration sensor 16 from the output reference value θ stored as a map in the ECU 37 is incorporated into the calibration coefficient A. If this deviation from the reference is excessively remarkable, then it can be determined that the oxygen concentration sensor 16 is faulty. If the coefficient falls within the predetermined range in step 610, then the sensor is considered to be fully operational (step 620). If the coefficient falls outside the range, then the sensor is considered to be faulty (step 630).

In the above embodiment, the vacuum sensor 15 functions as intake passageway pressure detection means that detects the intake passageway pressure in the intake passageway 4. Further, the ECU 37 functions as stable condition detection means, calibration coefficient detection means, calibration means, and calibration coefficient correction means. The air-fuel ratio sensor 28 functions as air-fuel ratio calibration means. The charcoal canister 34, purge control valve 35, and the ECU 37 function as fuel vapor purge means. In addition, the ECU 37, the coolant temperature sensor 26 and the like function as warm-up completion determination means.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are shown in various combinations and configurations, which are exemplary, other combinations and configurations, including more, less or only a single embodiment, are also within the spirit and scope of the present invention.

What is claimed is:

1. An intake air oxygen concentration sensor calibration device comprising:

an oxygen concentration sensor provided in a prescribed arrangement along an intake passageway of an internal combustion engine to detect a concentration of oxygen contained in intake air;

intake passageway pressure detection means that detects pressure in the intake passageway;

stable condition determination means that compares the amplitude of fluctuations in intake passageway pressure detected by the intake passageway pressure detection means with a predetermined stable condition criterion value previously stored in memory to determine whether the intake passageway pressure is in a stable condition;

calibration coefficient calculation means that calculates a calibration coefficient used to calibrate an output of the oxygen concentration sensor based on the intake passageway pressure detected by the intake passageway pressure detection means and a reference output value of the oxygen concentration sensor previously stored in memory; and calibration means that calibrates the output of the oxygen concentration sensor based on the calibration coefficient calculated by the calibration coefficient calculation means, wherein, the stable condition criterion value is set so that the smaller the intake passageway pressure detected by the intake passageway pressure detection means, the smaller the stable condition criterion value, and the greater the intake passageway pressure detected by the intake passageway pressure detection means, the greater the stable condition criterion value, and the calibration coefficient calculation means updates the calibration coefficient when the stable condition determination means determines that the intake passageway pressure is stable.

2. A calibration method for an oxygen concentration sensor provided in a prescribed arrangement along an intake passageway of an internal combustion engine to detect a concentration of oxygen contained in intake air, comprising the steps of:

detecting pressure in the intake passageway;

comparing the amplitude of fluctuations in detected intake passageway pressure with a predetermined stable condition criterion value previously stored in memory to determine whether the intake passageway pressure is in a stable condition;

calculating a calibration coefficient used to calibrate an output of the oxygen concentration sensor based on the detected intake passageway and a reference output value of the oxygen concentration sensor previously stored in memory; and calibrating the output of the oxygen concentration sensor based on the calculated calibration coefficient calculated, wherein, the stable condition criterion value is set so that the smaller the detected intake passageway pressure, the smaller the stable condition criterion value, and the greater the detected intake passageway pressure, the greater the stable condition criterion value, and wherein the calibration coefficient is updated when the intake passageway pressure is stable is determined.

3. An intake air oxygen concentration sensor calibration device comprising:

an oxygen concentration sensor provided in a prescribed arrangement along an intake passageway of an internal combustion engine to detect a concentration of oxygen contained in intake air;

an intake passageway pressure detector that detects pressure in the intake passageway; and a controller that compares the amplitude of fluctuations in intake passageway pressure detected by the intake passageway pressure detector with a predetermined stable condition criterion value previously stored in memory to determine whether the intake passageway pressure is in a stable condition, calculates a calibration coefficient used to calibrate an output of the oxygen concentration sensor based on the intake passageway pressure detected by the intake passageway pressure detector and a reference output value of the oxygen concentration sensor previously stored in memory, and calibrates the output of the oxygen concentration sensor based on the calculated calibration coefficient, wherein, the stable condition criterion value is set so that the smaller the intake passageway pressure detected by the intake passageway pressure detector, the smaller the stable condition criterion value, and the greater the intake passageway pressure detected by the intake passageway pressure detector, the greater the stable condition criterion value, and wherein the controller updates the calibration coefficient when the stable condition determination means determines that the intake passageway pressure is stable.

* * * * *